United States Patent
Reinhardt et al.

(10) Patent No.: US 6,503,215 B1
(45) Date of Patent: Jan. 7, 2003

(54) BANDAGE FOR PARTS OF THE BODY

(76) Inventors: Holger C.W. Reinhardt, Margeritenstrasse 153, 47906 Kempen (DE); Hans B. Bauerfeind, Wiesenstrasse 18, 47906 Kempen (DE)

(*) Notice: Subject to any disclaimer, the term of this patent is extended or adjusted under 35 U.S.C. 154(b) by 0 days.

(21) Appl. No.: 09/601,472

(22) PCT Filed: Sep. 14, 1999

(86) PCT No.: PCT/EP99/06794
§ 371 (c)(1),
(2), (4) Date: Sep. 21, 2000

(87) PCT Pub. No.: WO00/32139
PCT Pub. Date: Jun. 8, 2000

(30) Foreign Application Priority Data

Dec. 3, 1998 (DE) .......................... 198 55 923

(51) Int. Cl.[7] .................................................. A61F 5/00
(52) U.S. Cl. .............................. 602/19; 602/41; 2/44; 128/96.1
(58) Field of Search ........................... 602/3.19–20, 23, 602/26, 41, 60, 61–63, 14; 2/44; 128/96.1

(56) References Cited

U.S. PATENT DOCUMENTS

| 3,096,760 A | 7/1963 | Nelkin |
| 5,500,959 A | 3/1996 | Yewer, Jr. |
| 5,785,671 A | 7/1998 | Striano |

FOREIGN PATENT DOCUMENTS

| DE | 43 37 354 | 5/1994 |
| WO | 94 09728 | 5/1994 |

*Primary Examiner*—Michael A. Brown
*Assistant Examiner*—Lalita M. Hamilton

(57) ABSTRACT

Bandage for parts of the body, which bandage can be drawn tight by means of at least one tightening strap whose one end is secured on the bandage and whose other end, a tensioning end, can be fixed to the bandage, the tightening strap being passed back and forth through deflection rings which are secured on the bandage at a distance from one another, with inclusion of a contraction area, in such a way that a tensile force exerted on the tensioning end of the tightening strap acts in the manner of a pulley on the contraction area and thus shortens the bandage.

4 Claims, 2 Drawing Sheets

BANDAGE FOR PARTS OF THE BODY

Figure 1:
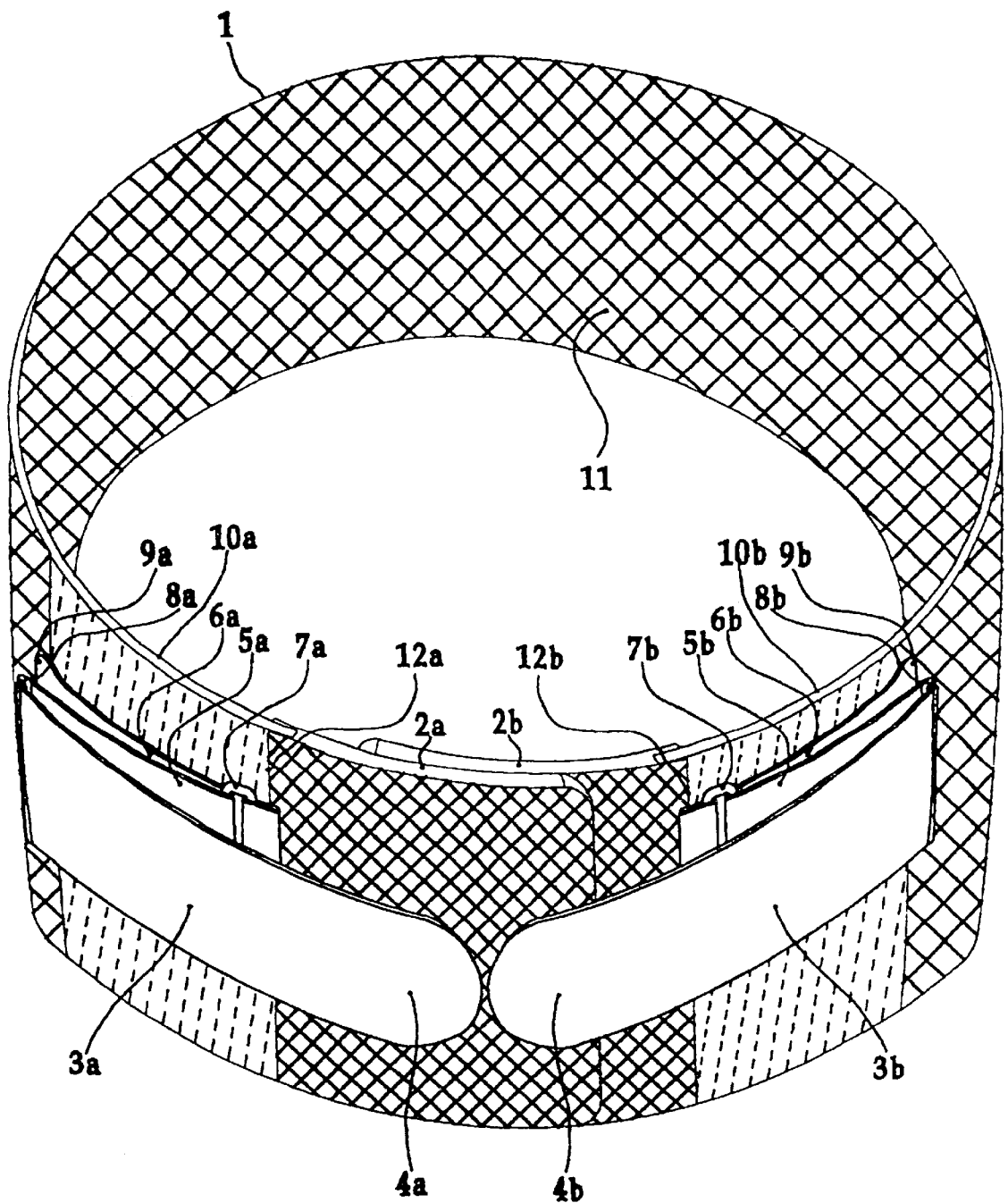

The invention relates to a bandage for parts of the body, which bandage can be drawn tight by means of at least one tightening strap whose one end is secured on the bandage and whose other end, a tensioning end, can be fixed to the bandage.

A bandage of this type is disclosed in German Laid-Open Patent Application 4,337,354. The known bandage consists of an abdominal belt which is closed via a fixing plate which serves to support the patient's back region. The connection between the fixing plate and the abdominal belt is effected by tightening straps which are each secured on the ends of the abdominal belt and are passed through openings in the fixing plate. By pulling on the free ends of the tightening straps, the bandage can then be adjusted to the girth of the body in question. The free ends of the tightening straps are then secured on the abdominal belt by means of closure elements.

A considerable tensioning force has to be exerted when applying bandages of this type, especially if the bandage is intended to exert a particularly strong support function. It is known that another person is often needed to help apply such bandages, since the patient concerned, because of his state of health, is not in a position to exert a sufficient tensioning force on the tightening straps.

The object of the invention is therefore to make it substantially easier to apply the bandage mentioned in the introduction, without the patient in question having to exert any particular force. According to the invention, this is achieved by means of a bandage design in which the tightening strap is guided back and forth through deflection rings which are secured on the bandage at a distance from one another, with inclusion of a contraction area, in such a way that a tensile force exerted on the tensioning end of the tightening strap acts in the manner of a pulley on the contraction area and thus shortens the bandage.

As a result of this arrangement of the deflector rings, in combination with the contraction area enclosed by them in the bandage, the tightening straps which draw the bandage tight are guided back and forth in the manner of a pulley system and can thus exert a high tensile force on the bandage, without the patient in question having to exert any particular effort to do this. With the bandage design according to the invention, the pulley system principle is thus elegantly incorporated into the bandage, as a result of which this bandage can even be applied by weakened persons without the assistance of other parties. This also affords the particular advantage that the patient is able to easily adapt the radial pressure exerted by the bandage by means of adjusting the tensile force, since the pulley system effect translates the tensile force exerted on the tightening straps to the tension exerted on the bandage.

The contraction area of the bandage is preferably made of an elastic material, whereas the other part of the bandage is made of a substantially less elastic material, in particular a nonelastic material. The advantage of this is that when the straps are pulled tight, the contraction area can draw together because of its elasticity, without folds being able to form in the contraction area.

In principle, it is sufficient for the bandage to be provided with just one contraction area and with the associated tightening straps. However, it is preferable for the bandage to be designed such that the contraction area with associated tightening strap or tightening straps is present twice in a symmetrical arrangement. In this case, the patient can pull with one hand on the tightening strap or tightening straps associated with one contraction area and thus correspondingly draw the contraction area together, which, in the case of two contraction areas of symmetrical arrangement, then results in a correspondingly great contraction, which acts laterally on both hips when the bandage is applied symmetrically on the body.

Figure 2:
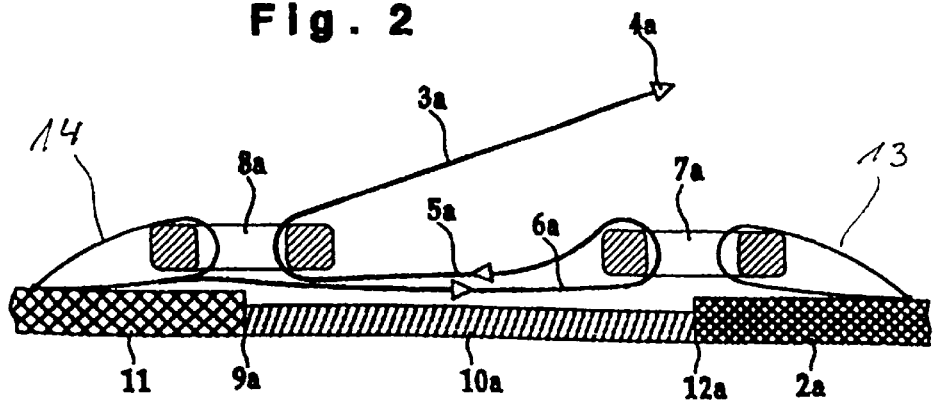
Figure 3:
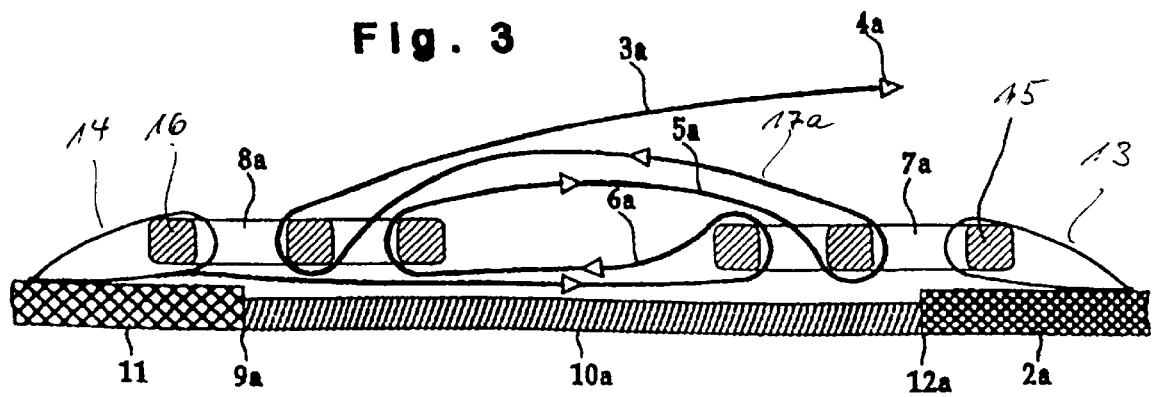
Figure 4:
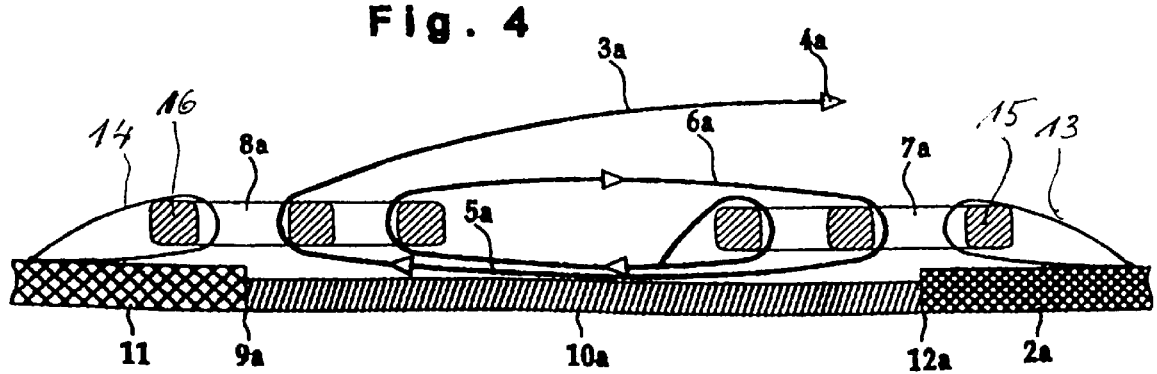

Illustrative embodiments of the invention are shown in the figures, where:

FIG. 1 shows the bandage in a perspective view, with two contraction areas in a symmetrical arrangement, FIG. 2 shows a diagrammatic representation of the guiding of the tightening straps in a contraction area according to FIG. 1, FIG. 3 shows a modification of the guiding of the tightening straps in which, compared to the representation in FIG. 2, additional deflection rings are provided for the purpose of multiplying the pulley system principle, and FIG. 4 shows a modification of the configuration in FIG. 3.

In FIG. 1, the bandage 1 is shown in a perspective view. It is closed by the two overlap areas 2a and 2b to form a ring. The two overlap areas 2a and 2b are designed in the manner of a velcro closure on their sides facing each other, so that the overlap areas 2a and 2b can be laid across one another to a greater or lesser extent depending on the size of the part of the body to be treated, in which position they are then secured to each other by means of the velcro closure provided between them.

It should be noted, however, that the bandage 1 can of course also be produced from a single continuous piece of material, but in this case it cannot be adapted in an especially simple way to the particular size of the part of the body in question.

Arranged next to the two overlap areas 2a and 2b are the contraction areas 10a and 10b, which merge into the rear curving part 11 of the bandage 1. The contraction areas are made of an elastic textile material, whereas the rest of the bandage, that is to say the two overlap areas 2a and 2b and the curving part 11, are made of a substantially nonelastic textile material.

One end 9a, 9b of the tightening strap 3a, 3b is secured in the area of the transition from the contraction area 10a, 10b to the rear curving part 11. From this end 9a, 9b, the length 6a, 6b of the tightening strap 3a, 3b extends to the deflection ring 7a, 7b, from which the tightening strap 3a, 3b is guided via the length 5a, 5b to the further deflection ring 8a, 8b. As a result of a further deflection of the tightening strap 3a, 3b via the deflection ring 8a, 8b, the tightening strap 3a, 3b with its tensioning end 4a, 4b then reaches the front middle area of the bandage 1, that is to say the overlap area 2a to which the tensioning end 4a, 4b can be fixed. To do this, use is made of a velcro closure arranged between the tensioning end 4a, 4b and the outside of the overlap area 2a.

After the bandage 1 has been applied, for example around a patient's hips, and the overlap areas 2a and 2b have been closed, the patient can pull with one hand on each of the tensioning ends 4a, 4b of the tightening straps 3a, 3b. If he has applied the bandage 1 in such a way that the overlap areas 2a and 2b lie on the surface of the body with the navel, then the two tensioning ends 4a and 4b can each be easily gripped by the patient by one hand and pulled forwards. The two-fold deflection per tightening strap 3a, 3b via the deflection rings 7a and 8a or 7b and 8b, as is chosen in the illustrative embodiment shown, results in a greater tensioning length for the respective tensioning end 4a, 4b relative to the approximation of the two deflection rings 7a and 8a or 7b and 8b, which results in a corresponding strengthening of the tension from the deflection ring 7a, 7b to the length 6a, 6b of the tightening strap 3a, 3b, as is known from the pulley system principle. As a result of the deflection ring 7a, 7b being secured at the transition point 12a, 12b between the contraction area 10a, 10b and the overlap area 2a, 2b, the contraction area 10a, 10b is drawn together, and the bandage 1 is drawn correspondingly tightly around the part of the body in question, that is to say in this case the patient's hips. After the contraction area 10a, 10b has been drawn together in this way, the ends 4a, 4b of the tightening straps 3a, 3b are then fixed, by means of the abovementioned velcro closure, to the outside of the overlap area 2a and the bandage 1 retains its tight fit on the body part in question.

The deflection rings 8a, 8b and 7a, 7b secured on the one hand at the area 9a, 9b and at the transition points 12a, 12b enclose between them the respective contraction area 10a, 10b, so that the tensile force applied when the tensioning ends 4a, 4b are pulled intensifies the drawing-together of the contraction area 10a, 10b.

The tightening straps 3a, 3b are made of a substantially nonelastic textile material. They can of course also have a certain elasticity, but this is not necessary for the correct functioning of the bandage according to the invention. The deflection rings 7a, 7b, 8a, 8b are here designed as elongate eyelets in order to provide favourable guides for the flat tightening straps 3a, 3b. Instead of in each case one tightening strap 3a, 3b with one contraction area 10a, 10b, it is of course also possible to arrange a plurality of tightening straps on a contraction area, which is particularly favourable when the bandage is a relatively wide one. Elongate deflection rings are shown, for example, in German Laid-Open Patent Application 4,337,354 mentioned in the introduction.

In the illustrative embodiment shown in FIG. 1, a symmetrical arrangement of two contraction areas 10a and 10b is deliberately provided. This is particularly of advantage for applying the bandage 1 using two hands. However, it should be noted that the bandage can of course also be equipped with just one contraction area, which single contraction area may be sufficient in particular in bandages for smaller parts of the body.

FIG. 2 is a diagrammatic representation, in a view towards the edge of the bandage 1, of the contraction area 10a which merges at one end into the curving part 11 and at the other end into the overlap area 2a. The two deflection rings 7a and 8a are shown in section. They serve on the one hand to deflect the tightening strap 3a with its lengths 5a and 6a, and on the other hand to secure the deflection ring 8a to the material of the curving part 11 near the end 9a of the bandage 3a (loop 14) and to secure the deflection ring 7a near the transition area 12a between contraction area 10a and overlap area 2a (loop 13).

FIG. 2 shows particularly clearly how, when the tensioning end 4a is pulled in the arrow direction indicated, the length 5a follows and thus draws the deflection ring 7a closer to the deflection ring 8a, with the length 6a being correspondingly shortened, as a result of which the contraction area 10a is correspondingly drawn together.

In the illustrative embodiment shown in FIG. 1, the tightening strap 3a, 3b is guided via a two-fold deflection, namely via the deflection rings 7a, 7b and 8a, 8b. It is also possible to guide each tightening strap via more than two deflections, in order thereby, in the manner of a pulley system, to further intensify the tensioning effect when the tensioning ends of the tightening straps are pulled.

FIG. 3 shows a view similar to that in FIG. 2, showing, in a section from the bandage (as is also shown in FIG. 2) the contraction area 10a and, in section, the curving part 11 and the overlap area 2a. In addition to the two lengths 5a and 6a shown in FIG. 2, the embodiment according to FIG. 3 is provided with a further length 17a, so that in all there are four deflections through which the pulley system effect, when the tensioning end 4a is pulled, exerts a corresponding contraction force on the contraction area 10a. The deflection rings 7a and 8a are each provided with three rungs in this embodiment, the outer rung 15 or 16 serving for securing via the loop 14 or 15, respectively.

FIG. 4 shows a modification of the embodiment according to FIG. 3, in which modification a plurality of deflections are likewise provided, and where the tightening strap 3a, as in the embodiment according to FIG. 2, is divided into the two lengths 5a and 6a, but in this case is deflected three times, as a result of which, again compared to the arrangement according to FIG. 2, the contraction force which draws the contraction area 10a together is intensified.

What is claimed is:

1. Bandage (1) for parts of the body, which bandage can be drawn tight by means of at least one tightening strap (3a, 3b) whose one end (9a, 9b) is secured on the bandage (1) and whose other end, a tensioning end (4a, 4b), can be fixed to the bandage (1), characterized in that the tightening strap (3a, 3b) is guided back and forth through deflection rings (7a, 7b; 8a, 8b) which are secured on the bandage at a distance from one another, with a contraction area (10a, 10b) between the rings, in such a way that a tensile force exerted on the tensioning end (4a, 4b) of the tightening strap (3a, 3b) acts in the manner of a pulley on the contraction area (10a, 10b) and thus shortens the bandage (1).

2. Bandage (1) according to claim 1, characterized in that the contraction area (10a, 10b) is made of an elastic material and the other part of the bandage (1) is made of a substantially less elastic material.

3. Bandage (1) according to claim 1 or 2, wherein the bandage includes a plurality of symmetrically oriented contraction areas and tightening straps.

4. Bandage (1) according to claim 1 wherein the less elastic material of the other part of the bandage is a nonelastic material.

* * * * *